United States Patent
Brown, Jr.

(10) Patent No.: US 6,939,366 B2
(45) Date of Patent: Sep. 6, 2005

(54) SUN BATHING AND SAUNA ASSEMBLY

(76) Inventor: John N. Brown, Jr., 5104 Charbdin Ct., Louisville, KY (US) 40207

( * ) Notice: Subject to any disclaimer, the term of this patent is extended or adjusted under 35 U.S.C. 154(b) by 230 days.

(21) Appl. No.: 10/370,217

(22) Filed: Feb. 21, 2003

(65) Prior Publication Data

US 2004/0167591 A1 Aug. 26, 2004

(51) Int. Cl.$^7$ ............................................. A61N 5/06
(52) U.S. Cl. ........................... 607/95; 607/96; 607/107; D23/315; D23/317; D24/203; D24/204
(58) Field of Search ............................ 607/95, 96, 107; D23/315, 317; D24/203, 204

(56) References Cited

U.S. PATENT DOCUMENTS

| | | | |
|---|---|---|---|
| 3,170,172 A | 2/1965 | Kessman | |
| 3,688,775 A | 9/1972 | Rayman | |
| 4,320,744 A | * 3/1982 | Fodor et al. | 126/570 |
| 4,525,884 A | 7/1985 | Tolley | 5/243 |
| 4,640,284 A | * 2/1987 | Ruderian | 607/96 |
| 4,712,538 A | * 12/1987 | Hardie et al. | 601/16 |
| 4,739,763 A | 4/1988 | Parsell | 128/372 |
| D297,863 S | * 9/1988 | Hardie et al. | D24/37 |
| D313,847 S | * 1/1991 | Higgins | D24/39 |
| 4,989,600 A | 2/1991 | Collier | 128/372 |
| 5,085,212 A | * 2/1992 | DeCosta | 607/95 |
| 5,101,823 A | 4/1992 | Smith | 128/369 |
| 5,733,314 A | 3/1998 | Perrino | 607/91 |
| 5,879,377 A | 3/1999 | Mullins | 607/95 |
| 6,585,751 B1 | * 7/2003 | Silverman | 607/95 |
| 6,629,964 B1 | * 10/2003 | Ono et al. | 604/304 |

FOREIGN PATENT DOCUMENTS

| JP | 01033463 | * 2/1989 | 126/369 |
|---|---|---|---|

* cited by examiner

*Primary Examiner*—A. Farah
(74) *Attorney, Agent, or Firm*—Berenato, White & Stavish, LLC

(57) ABSTRACT

An assembly for use as a sun bathing spa and as a sauna, which is constructed of light weight materials, so as to be portable for use in a yard outside of and near to a residence or otherwise and which includes an air conditioning system for comfort of a person lying prone within a frame of the assembly. A heat transfer unit is disposed in a first end member of the assembly for providing warm or cooling air as the case may be, which can be directed by blowers through air passageways in side members of the assembly to be directed across the body of the person lying within a frame of the assembly to comfort the person in both low temperature and high temperature ambient environments. Transparent and foam covers can be used over the assembly to convert the latter from a sun bathing spa to a sauna.

15 Claims, 5 Drawing Sheets

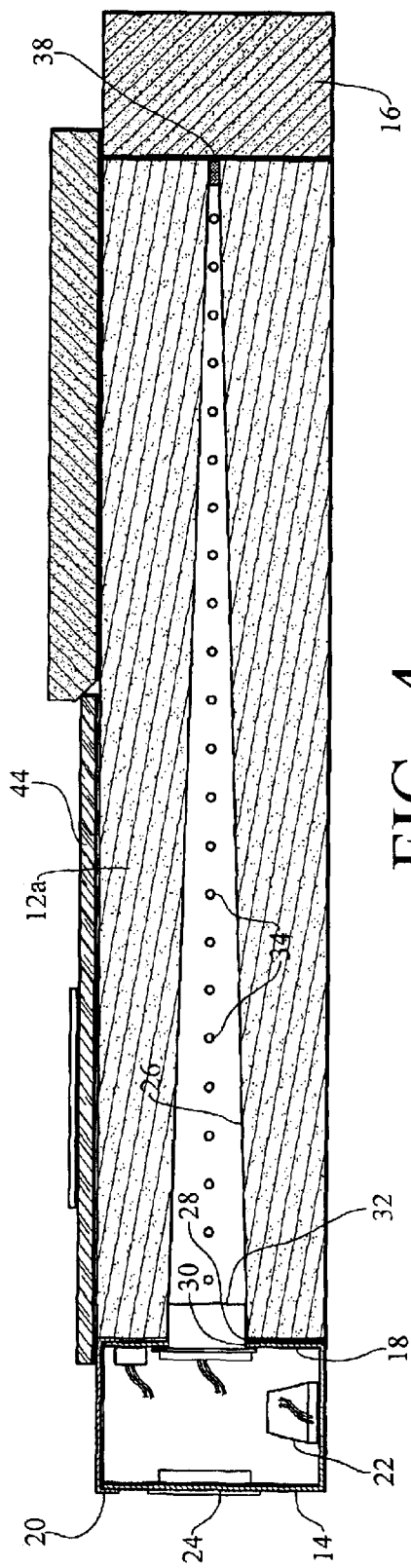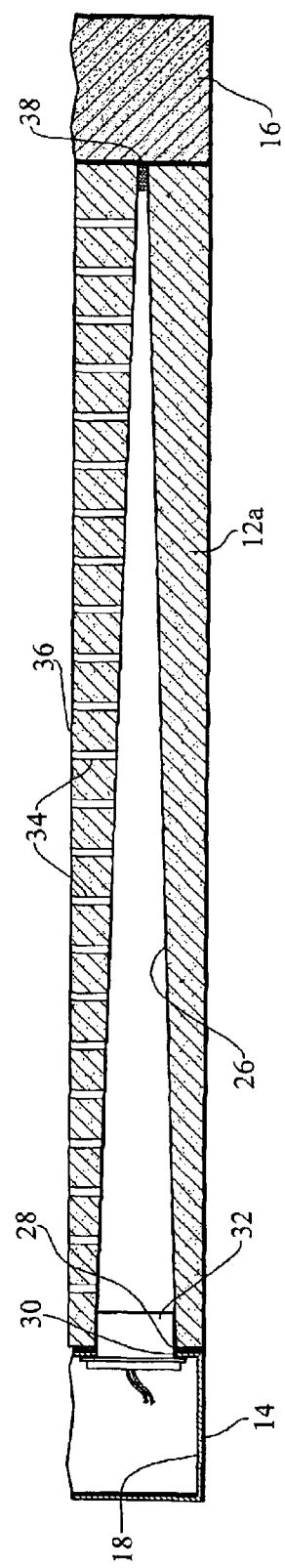

SUN BATHING AND SAUNA ASSEMBLY

BACKGROUND OF THE INVENTION

This invention relates to a portable sun tanning spa and sauna assembly which can provide either comforting heated or dehumidified forced air flow across the body of a person lying within the assembly depending upon ambient atmospheric temperatures.

Various sun bathing and sauna assemblies are known in the prior art. See, for example, the sun bathing and tanning devices disclosed in U.S. Pat. No. 3,170,172 granted to L. P. Kessman on Feb. 23, 1965 and U.S. Pat. No. 5,879,377 granted to C. Mullins on Mar. 9, 1999. The Kessman sun tanning device is adapted to allow direct tanning of one side of a sun bather's body while permitting reflected sun light to tan the opposite side. The Mullins assembly comprises a bed tray for sun tanning which holds a quantity of water for cooling the body of a person lying within the tray. U.S. Pat. No. 5,101,823 granted to G. Smith on Apr. 7, 1992 also shows a tanning bed adapted to hold a quantity of cooling water for the comfort of a sun bather. Finally, U.S. Pat. No. 4,739,763 granted to I. L. Parsell on Apr. 26, 1988 and U.S. Pat. No. 4,989,600 granted to J. M Collier on Feb. 5, 1991 disclose solar heated sauna assemblies. The collier patent is directed to a pod forming a body shell including a transparent dome. The pod contains a bed which is tiltable by means of a motor and a self contained climate control system. The pod itself can be rotatably adjusted by means of a motor. The device of Collier is a complex structure and, while adapted for use outside in different types of weather conditions, is not readily portable. It is also quite clearly an elaborate and relatively expensive structure. Finally, the Collier device is not adapted for use in direct sunlight absent the transparent dome.

Accordingly, it would be desirable to provide a sun tanning assembly which can also be used as a sauna and which can provide air conditioning for the comfort of the user in a light weight, highly portable, inexpensive assembly not heretofore known in the prior art. By means of my invention, these and other important objectives can be obtained.

SUMMARY OF THE INVENTION

Briefly, in accordance with the present invention, there is provided a sun tanning spa and sauna assembly comprising a frame. The frame includes a pair of spaced apart side members constructed of a light weight foam material having first and second corresponding ends. Each of the side members defines a longitudinally extending major air passageway opening on an inlet end of a different one of the first corresponding ends. Each major air passageway is closed on an opposite, downstream end. Each of the side members further defines a series of transversely extending, spaced apart minor air passageways which communicate with a corresponding major air passageway and which open on a side wall which opposes a side wall of the other of the side members. The assembly further comprises a first end member having a hollow interior chamber, which first end member adjoins the first corresponding ends of the side members. The assembly also includes a second end member constructed of a light weight foam material, which second end member adjoins the second corresponding ends of the side members such that the members enclose all sides of the frame. The assembly additionally comprises an air heat transfer unit disposed in the interior chamber of the first end member and an air intake vent attached to the first end member for introducing ambient air into the interior chamber of the first end member to be conditioned by the heat transfer unit. The assembly also comprises a pair of motorized blowers, each of the blowers being mounted on the first end member for introducing air conditioned air into the inlet end of the major air passageway of a different one of the side members. The frame is sized to permit a person to recline therein between the side members such that air, conditioned by the heat transfer unit, can be expelled from the minor air passageways across the body of the person.

These and other objects, features and advantages of the present invention will become apparent to those skilled in the art from the following detailed description and attached drawings upon which, by way of example, only a preferred embodiment of my invention is illustrated.

BRIEF DESCRIPTION OF THE DRAWINGS

FIG. 4 shows a cross-section view of yet another portion of the assembly and cover of FIGS. 1a, 2 and 3 as viewed along cross-section lines 4—4 of the latter mentioned figure with certain absent parts of FIG. 3 being replaced.

FIG. 5 shows a cross-sectional downward view of a portion of the assembly of FIGS. 1–4 as viewed along cross-section lines 5—5 of FIG. 1a.

DESCRIPTION OF THE PREFERRED EMBODIMENT

Figure 1:
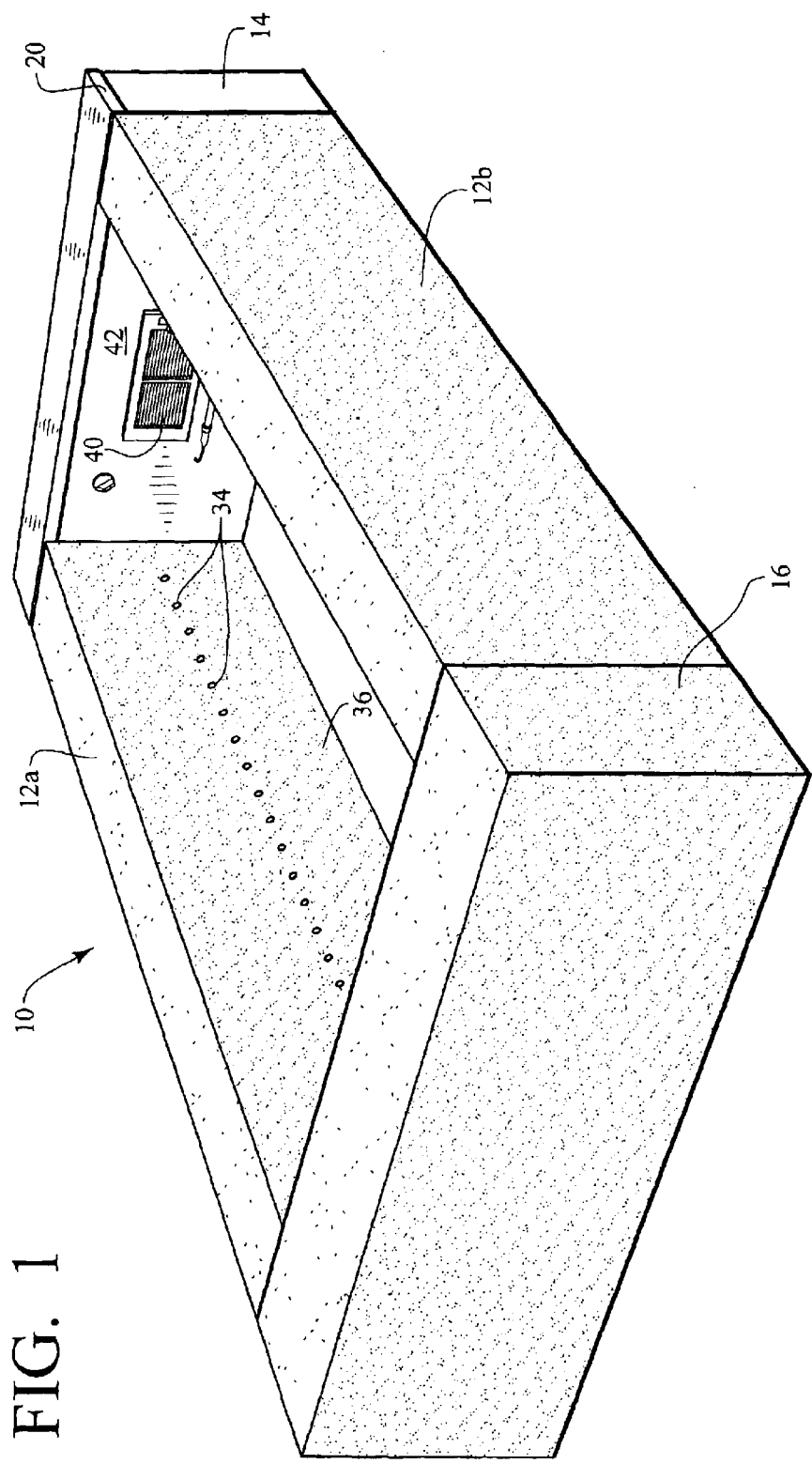
FIG. 1 shows a perspective view of an air conditioned sun tanning and sauna assembly, thus illustrating a preferred embodiment of my invention.
Figure 1A:
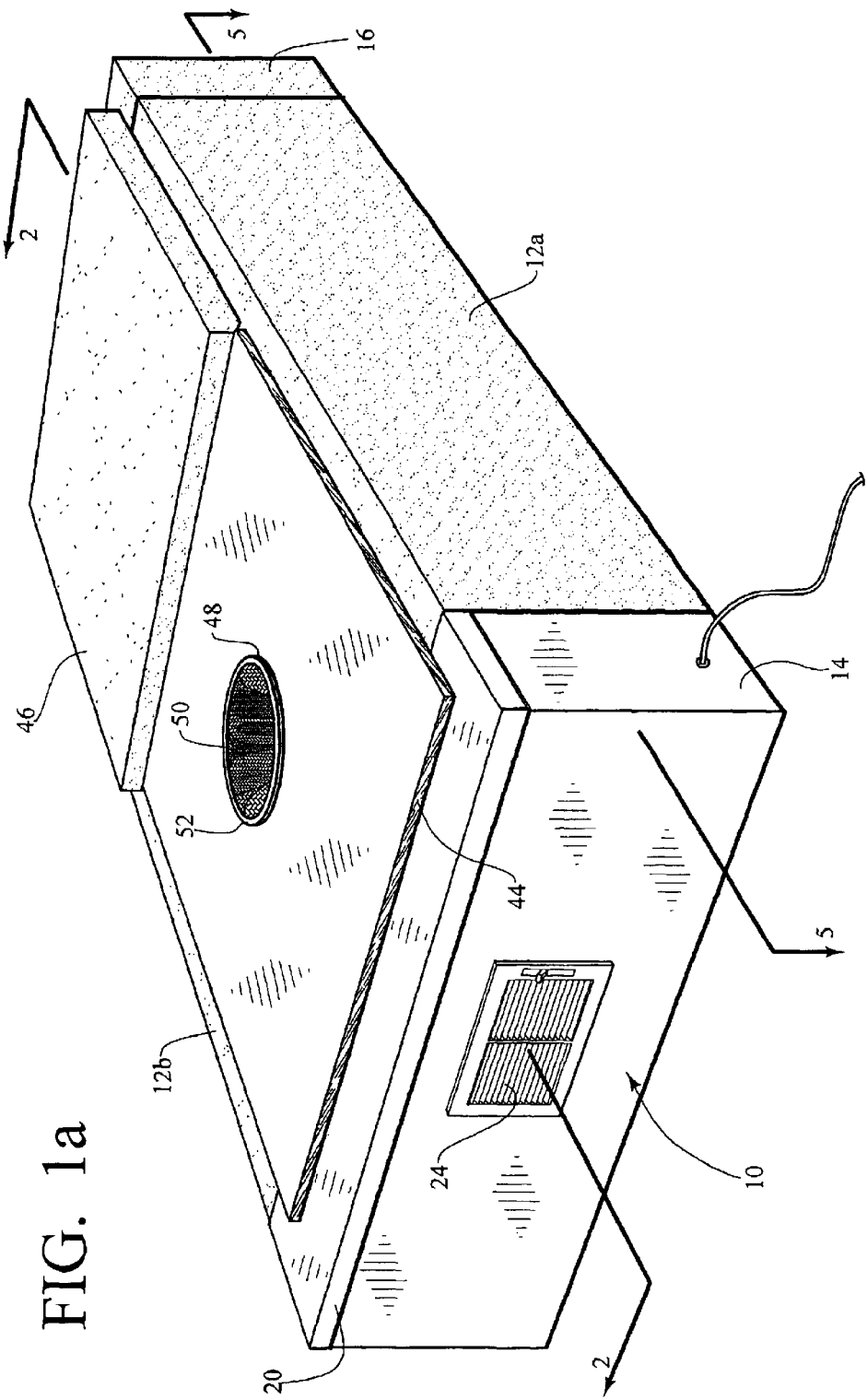
FIG. 1a shows another perspective view of the assembly of FIG. 1 as seen from another orientation and additionally includes a frame cover for use as an outdoor sauna.
Figure 2:
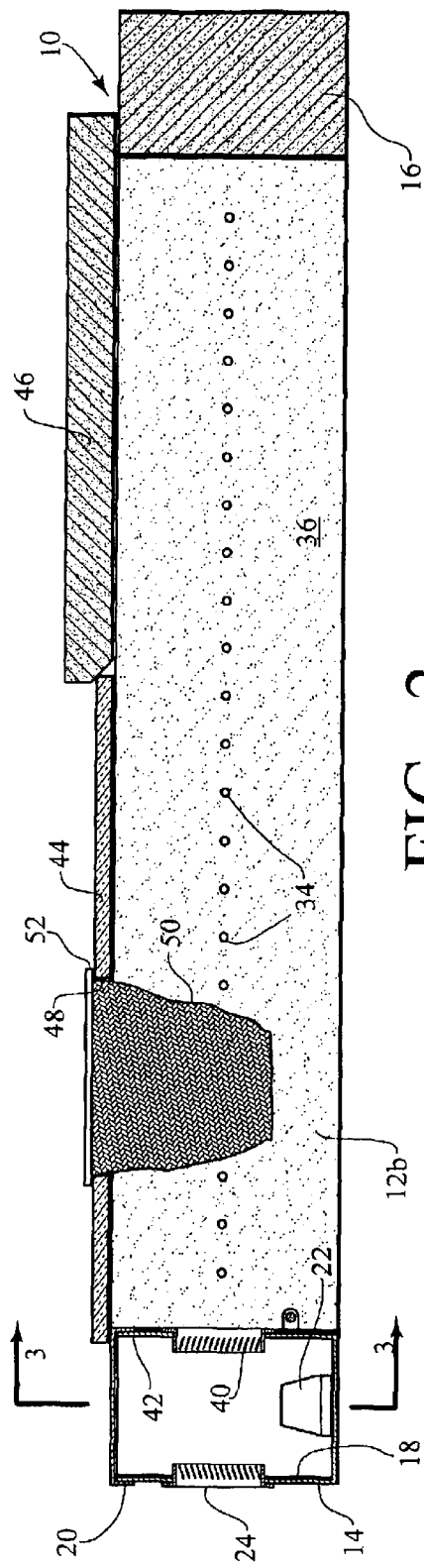
FIG. 2 shows a cross-sectional view of a portion of the assembly and cover of FIG. 1a as viewed along cross-section lines 2—2 of the latter mentioned figure.

Referring now to the drawing figures, there is shown, in a preferred embodiment of my invention, an air conditioned sun tanning spa and sauna assembly, generally designated 10 for use in a yard outside of and near a residence or otherwise. As best shown in FIG. 1, the assembly 10 comprises a frame including a pair of spaced apart side members 12a, 12b, a first end member 14 having opposite side portions which adjoin first corresponding ends of the side members and a second end member 16 having opposite side portions which adjoin second corresponding ends of the side members. The members 12a, 12b, 14 and 16 completely enclose all sides of the frame and, preferably, form a generally rectangularly shaped frame, sized to fit around a person when reclined in the frame in a prone position. The side members 12a, 12b and the second end member 16 are constructed of a light weight foam material such as, for example, expanded polystyrene. The first end member 14 contains a hollow interior chamber 18 (See FIGS. 2–3) and is preferably constructed of a lightweight material such as metal or plastic or other suitable material which is not capable of burning or melting at temperatures of 200° F. and below. The members 12a, 12b, 14 and 16 need not be fastened together and can simply be placed against one another as shown for operation of the assembly 10. Accordingly, the members 12a, 12b, 14 and 16 can be individually moved from one place to another and can be conveniently stored as, for example, by stacking. In the preferred embodiment, the first end member 14 is constructed in the form of an open top box and includes a lid or removable cover 20 capable of completely enclosing the chamber 18.

The interior chamber 18 of the first end member 14 contains a conventional heat transfer unit 22 which may be either an air heating unit or a dehumidifying coil or both for use, depending on whether the assembly 10 is to be used in cold weather or warm weather. The first end member 14 also includes and air intake vent 24 attached thereto for introducing ambient air into the chamber 18 to be appropriately conditioned by the heat transfer unit 22. The side members 12a, 12b each define a longitudinally extending major air passageway 26 (See FIGS. 4–5) opening on an inlet end 28 of a different one of the first corresponding ends. The inlet ends 28 register with openings 30 formed on opposite side portions of an inner facing wall of the first end member 14. A pair of conventional motorized blowers 32, which may be in the form of rotary fans, are disposed in the inlet ends 28 of the major air passageways 26 and are mounted on the inner facing wall around the openings 30 of the first end member 14. Each of the side members 12a, 12b also define a series of transversely extending and longitudinally spaced apart minor air passageways 34 which communicate on first corresponding ends with the corresponding major air passageway 26 and which open on second corresponding ends on a side wall 36 (See FIGS. 1–2 and 5) into an interior open space in the frame, which side wall opposes an interior side wall 36 of the other of the side members. Thus, air, which has been conditioned by the heat transfer unit 22, is introduced into the major air passageways 26 from the interior chamber 18, by the blowers 32, into the minor air passageways 34 to be blown across a central open space between the side members 12a and 12b across the body of a person lying within the frame.

As shown in FIGS. 4–5, the major air passageways 26 of each of the side members 12a and 12b are preferably cone shaped so as to have a maximum diameter at the inlet ends 28 and so as to gradually taper to a minimum diameter at opposite, downstream ends 38. The second end member 16 effectively closes off the downstream ends 38 so that all of the conditioned air introduced into the inlet ends 28 flows more or less evenly out of the various minor air passageways 34 of both of the side members 12a and 12b into the central open space in the frame. The cone shaped passageways 26 can be formed in any conventional, well known manner such as by stringing a heatable wire through a mold for each of the side members 12a and 12b which is fixed at opposite ends during the foam curing process. After the foam is satisfactorily cured, the wires are freed at their inlet ends 28 and are heated from the downstream ends 38 sufficient to melt the cured foam on contact. The wires on the inlet ends 28 are held taught while being rotated in a circular pattern at the inlet ends 28 to melt foam and carve out the preferred cone shaped passageways 26. Thereafter, the wires are cooled and are subsequently removed from the side members 12a and 12b. The downstream ends 38 of the major air passageways 26 can be sealed in any suitable manner as by means of polystyrene plugs. See FIGS. 4–5.

To obtain more air, conditioned by the heat transfer unit 22, in the interior open space of the frame from the chamber 18 than is delivered from the minor air passageways 34 alone, a second, adjustable air vent 40, mounted on an interior facing wall 42 of the first end member 14 is opened. The air vent 40 can also operate to recirculate air from the interior open space of the frame back into the chamber 18 for conditioning by the heat transfer unit 22.

Figure 2A:
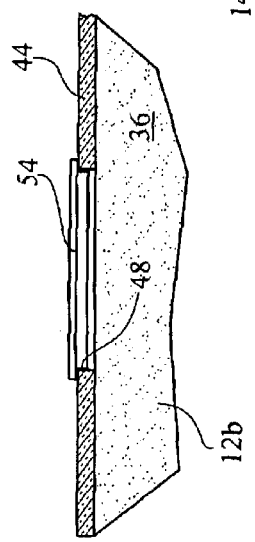
FIG. 2a shows a fragment of the portion of FIG. 2 wherein a breathing sock in a cover plate is replaced by a disc shaped cap.

When used as a sauna, the assembly 10 also includes a transparent cover 44, preferably made of a lightweight plastic, which is adapted to rest on the upper surfaces of the first end member 14 and the side members 12a and 12b. The cover 44 covers an upper portion of the body of a person reclined within the frame so as to allow warming sunlight to enter the interior open space and to permit external viewing by an occupant of the frame. A lower portion of the interior open space next to the transparent cover 44 is covered by a lightweight foam cover 46 which acts as an insulator to trap heat within the interior open space. The transparent cover 44 includes a circular opening 48 in which a flexible cloth breathing sock 50, suspended from a rigid circular rim 52, is mounted. The opening 48 is located at the head level of a person lying within the frame so that the sock 50 can be placed over the person's face to allow breathing of ambient air when the covers 44 and 46 are operatively positioned. When the sock 50 is not used, as where the air vents 34 and 40 are open, a lightweight transparent cap 54 (See FIG. 2a) may be placed in the opening 48 upon removal of the sock 50 and rim 52. The light weight covers 44 and 46 are easily adjustable in position over the frame by a person lying within the latter.

Figure 6:
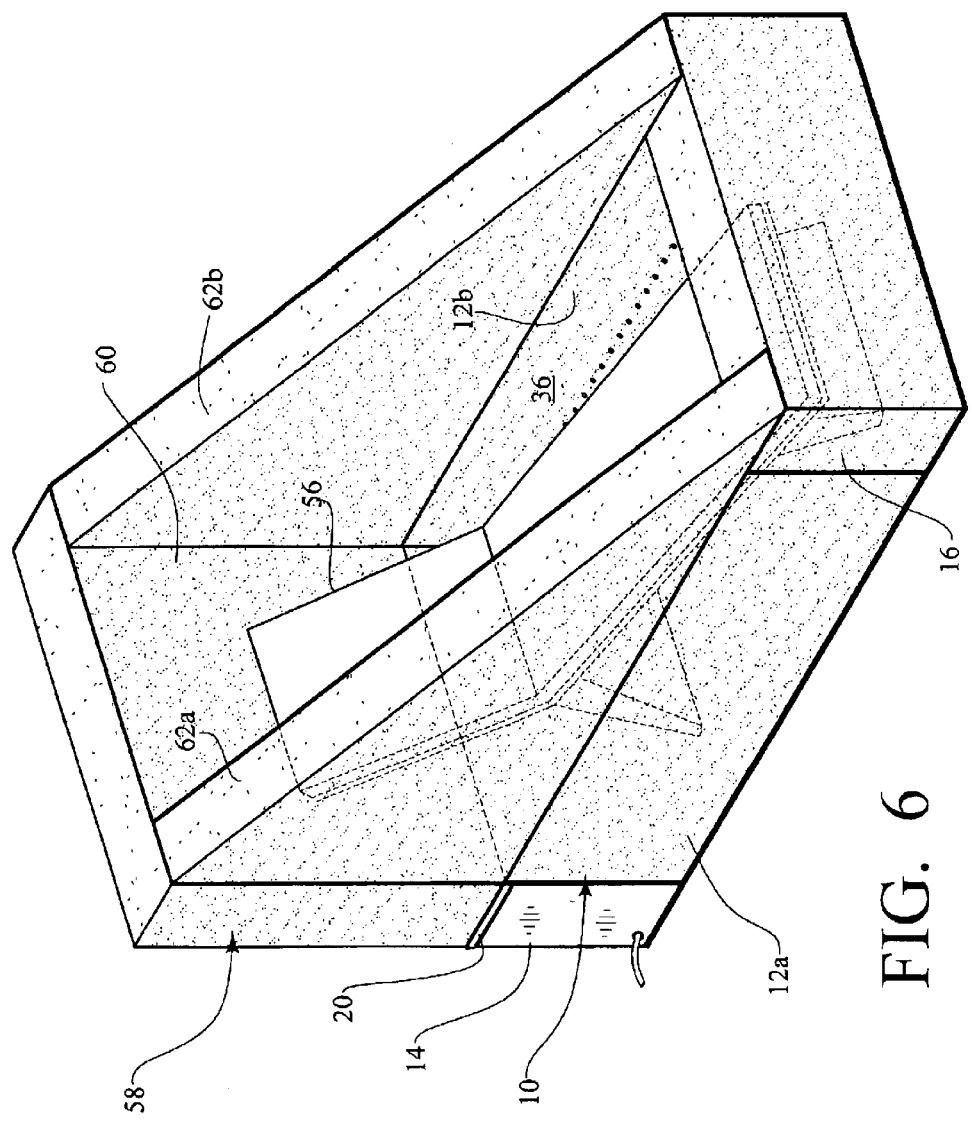
FIG. 6 shows an isometric view of the assembly of FIGS. 1–5 including a three sided wall structure mounted thereon.

Referring now particularly to FIG. 6, the assembly 10, is sized to contain a beach or lawn lounge chair 56, is shown. A three sided raised wall structure, generally designated 58, and, preferably, constructed of a lightweight material, such as foam, plastic, wood or metal, rests on upper surfaces of the members 12a, 12b, 14 and 16. The wall structure 58 includes a rectangularly shaped wall or head board 60, which rests on the cover 20 of the first end member 14, and two adjacent triangularly shaped side walls 62a and 62b. The side walls 62a and 62b rest upon upper surfaces of opposite side portions of second end member 16 and extend along the upper surfaces of the side members 12a and 12b and across opposite side portions of the second end member 16. The head board 60 and sidewalls 62a, 62b need not be fastened together and can be individually positioned on the assembly 10 as shown. The wall structure 58 helps to temporarily confine air, conditioned by the heat transfer unit 22, within the frame of the assembly 10 for the comfort of a person sun bathing on the beach chair 56. It also helps to minimize ambient air flow into the frame.

Figure 3:
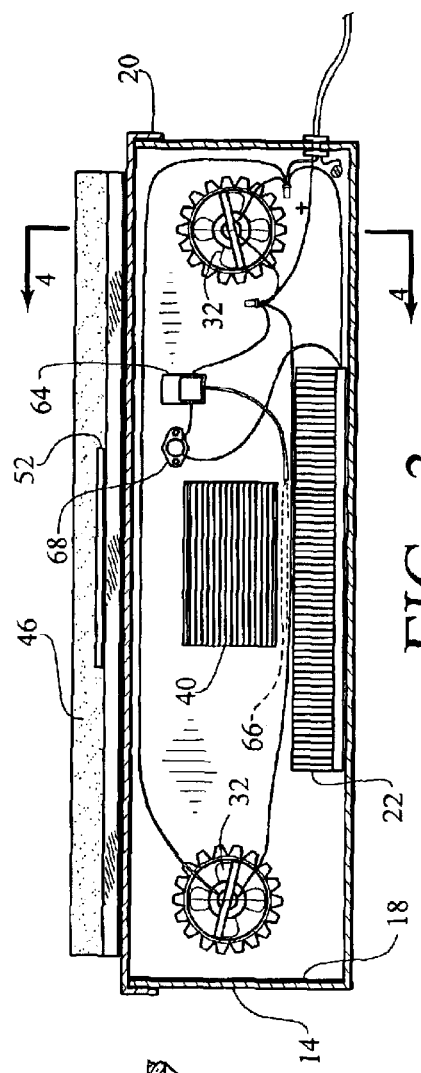
FIG. 3 shows a cross-sectional view of another portion of the assembly and cover of FIGS. 1a and 2 as viewed along cross-section lines 3—3 of the latter mentioned figure with certain absent parts of cross-sectioned FIG. 2 being replaced.

Referring to FIG. 3, where the heat transfer unit 22 comprises a space heater, it is shown as conveniently located under the vent 40. Also shown is a thermostat 64 including a temperature sensing bulb 66 See also FIG. 1). A standard temperature limit switch 68 is mounted on the first end member 14 for safety purposes which I recommend be set to turn off the heater 22 should the temperature in the interior chamber 18 of the first end member 14 increase to 180° F.

Although the present invention has been described and shown with respect to specific details of a certain preferred embodiment thereof, it is not intended that such details limit the scope and coverage of this invention other than as expressly set forth in the following claims, giving due consideration to reasonably equivalent structures.

I claim:

1. A sun tanning spa and sauna assembly comprising
   a frame including
   a pair of spaced apart side members constructed of a light weight foam material and having first and second corresponding ends, each of said side members defining a longitudinally extending major air passageway opening on an inlet end onto a different one of said first corresponding ends, said major air passageway being closed on an opposite end, each of said side members further defining a series of transversely extending, spaced apart minor air passageways communicating with said major air passageway and opening on a side wall opposing the other of said side members;
   a first end member having a hollow interior chamber adjoining said first corresponding ends; and
   a second end member constructed of a light weight foam material and adjoining said second corresponding ends such that side members,enclose all sides of said frame;
   an air heat transfer unit disposed in said interior chamber;
   an air intake vent attached to said first end member for introducing ambient air into said interior chamber to be conditioned by said heat transfer unit; and
   a pair of motorized blowers, each of said blowers being mounted on said first end member for introducing air, conditioned by said heat transfer unit, into the inlet end of the major air passageway of a different one of said side members, said frame being sized to permit a person to recline between said frame members such that air, conditioned by said heat transfer unit, can be expelled from said minor air passageways across the body of said person.

2. The assembly of claim 1 wherein said frame is generally rectangularly shaped.

3. The assembly of claim 1 wherein each of said members is rectangularly shaped in transverse cross section.

4. The assembly of claim 1 wherein the major passageway of each of said side members is cone-shaped wherein the inlet end has a maximum diameter and wherein the diameter of said cone is tapered downwardly from said maximum diameter moving from the inlet end to the opposite end.

5. The assembly of claim 1 wherein said first end member comprises a light weight material selected from the group consisting of metal or plastic.

6. The assembly of claim 1 wherein said first end member comprises a five sided container having an open upper side, said first end member further comprising a closure member removably disposed over said open upper side.

7. The assembly of claim 1 wherein said air heat transfer unit comprises an electrically operated air heating unit.

8. The assembly of claim 1 wherein said air heat transfer unit comprises an electrically operated air cooling coil.

9. The assembly of claim 1 wherein the foam material of which said side members are constructed comprises expanded polystyrene.

10. The assembly of claim 1 further comprising a transparent cover removably disposed over said frame, said cover including an opening and an air breathing sock attached to said cover around said opening for use by a person reclined in said frame under said cover.

11. The assembly of claim 1 further comprising a second air vent attached to said first end member for introducing air, conditioned by said heat transfer unit from said interior chamber into said frame between said side members.

12. The assembly of claim 1 wherein said second end member comprises expanded polystyrene.

13. The assembly of claim 1 wherein said blowers comprise electrically operated fans.

14. The assembly of claim 1 further comprising wall structure constructed of a lightweight foam material and including
   a rectangular shaped head board mounted on said first end member; and
   a pair of triangularly shaped side walls removably mounted on said side members with vertically extending sides of said side walls abutting opposite side portions of said head board.

15. The assembly of claim 14 wherein a central open area of said frame is sized to fit a beach side lounge chair.

* * * * *